United States Patent [19]

Teach

[11] Patent Number: 4,744,813

[45] Date of Patent: May 17, 1988

[54] HERBICIDAL IMIDAZOLIDINE-2-ONES AND METHODS OF USE

[75] Inventor: Eugene G. Teach, El Cerrito, Calif.

[73] Assignee: Stauffer Chemical Co., Westport, Conn.

[21] Appl. No.: 933,834

[22] Filed: Nov. 24, 1986

[51] Int. Cl.⁴ .................... A01N 43/50; C07D 233/70
[52] U.S. Cl. .......................................... 71/92; 548/322
[58] Field of Search ..................... 548/320, 322; 71/92

[56] References Cited

PUBLICATIONS

Chemical Abstracts, vol. 77, No. 19, Abstract 126631q, p. 402, Nov. 6, 1972.
Synerholm et al., *Journal of Organic Chemistry*, vol. 33, No. 3, Mar. 1968, (pp. 1111–1116).

*Primary Examiner*—Henry R. Jiles
*Assistant Examiner*—Zinna Northington
*Attorney, Agent, or Firm*—Paul R. Martin

[57] ABSTRACT

An imidazolidine-2-one having the formula

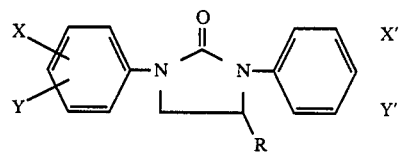

in which
X, X', Y and Y' are the same or different and are selected from the group consisting of trifluoromethyl, chloro, bromo, fluoro, hydrogen, cyano, alkyl, thioalkyl, halothialkyl, alkoxy and sulfonylalkyl, wherein the alkyl groups have from one to four carbon atoms; and
R is selected from the group consisting of hydrogen and alkyl wherein the alkyl groups have from one to four carbon atoms. The compounds are useful as herbicidal agents.

21 Claims, No Drawings

HERBICIDAL IMIDAZOLIDINE-2-ONES AND METHODS OF USE

BACKGROUND OF THE INVENTION

The present invention relates to certain imidazolidine-2-one compounds which are useful as pre-emergent and post-emergent herbicides against grasses and broadleaf weed species.

Herbicides are widely used by farmers, commercial agricultural companies, and other industries in order to increase crop yields for such staple crops as corn, soybeans, rice, and the like, and to eliminate weed growth along highways, railroad rights-of-way, and other areas. Herbicides are effective in killing or controlling unwanted weeds which compete for soil nutrients with the crop plants, and by reason of the fact that they kill weeds, are responsible for improving the aesthetic appearance of highway and railroad rights-of-way.

There are a number of different types of herbicides presently sold commercially, and these fall into two general categories. The categories are pre-emergence and post-emergence herbicides. The pre-emergence herbicides are normally incorporated into or applied to the soil prior to the emergence of the weed plants from the soil, and the post-emergence herbicides are normally applied to plant surfaces after emergence of the weeds or other unwanted plants from the soil.

Some herbicides are effective both as pre-emergence and post-emergence herbicides. The imidazolidine-2-ones of this invention fall into this category.

DESCRIPTION OF THE INVENTION

It has now been discovered that certain imidazolidine-2-ones have good herbicidal and plant growth regulating activity, particularly when applied as pre- or post-emergent herbicides and used against grasses or broadleaf weed species.

As used herein, the term "herbicide" means a compound or composition which controls or modifies the growth of plants. By the term "herbicidally effective amount" is meant any amount of such compound or composition which causes an adversely modifying effect upon the growth of plants. By "plants" is meant germinant seeds, emerging seedlings and established vegetation, including roots and above-ground portions. Such controlling or modifying effects include all deviations from natural development, such as killing, retardation, defoliation, desiccation, regulation, stunting, tillering, leaf burn, dwarfing and the like.

The imidazolidine-2-one compounds of this invention have the formula

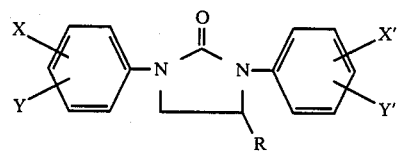

in which
X, X', Y and Y' are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups have from one to four carbon atoms; and R is selected from the group consisting of hydrogen and alkyl wherein the alkyl groups have from one to four carbon atoms.

The compositions of the invention comprise the aforementioned herbicide compounds, along with inert diluent carriers, as set forth more fully hereinbelow.

The method of the invention comprises the application to the locus where control is desired either the compounds or compositions containing the compounds described herein.

The compounds of this invention can prepared in accordance with a process which comprises:

(a) reacting an aryl substituted anilino alkanone having the formula

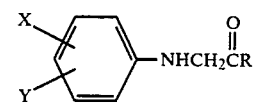

with an aryl substituted isocyanate of the formula

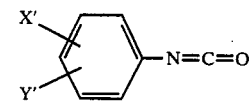

to form an intermediate imidazoline of the formula

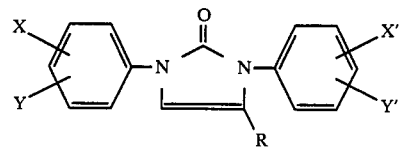

and (b) hydrogenating said intermediate imidazoline in the presence of a suitable catalyst to form the end product, an imidazolidine having the formula

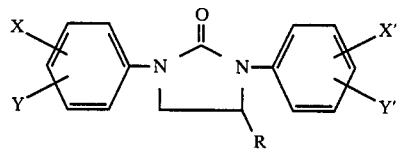

wherein
X, X', Y and Y' are the same or different and are selected from the group consisting of trifluoromethyl, chloro, bromo, fluoro, hydrogen, cyano, alkyl, thioalkyl, halothioalkyl, alkoxy and sulfonylalkyl wherein the alkyl groups have from 1 to 4 carbon atoms; and R is selected from the group consisting of hydrogen and alkyl wherein the alkyl groups have from 1 to 4 carbon atoms.

This reaction can be represented schematically as follows:

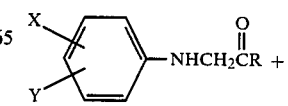

1.

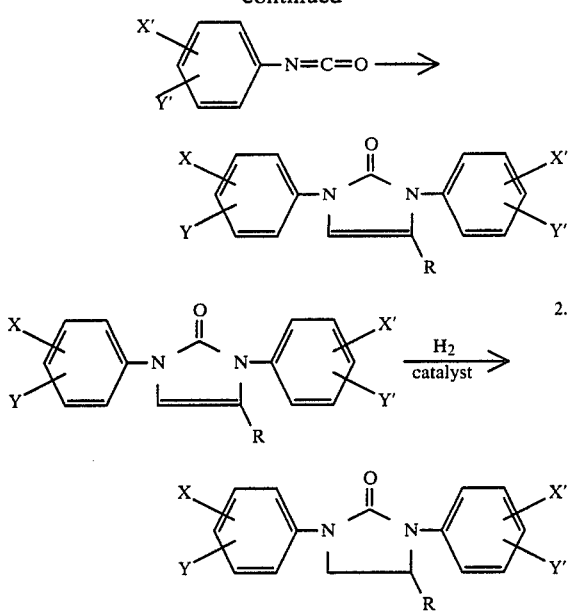

wherein X, X', Y, Y' and R are as defined above.

As indicated, the process is a two-step reaction, and can be terminated at the end of the first step, i.e., step (a), to isolate the imidazoline compounds which are also herbicidally active. These are new compounds and are disclosed and claimed in co-pending application Ser. No. 933,833, filed Nov. 24, 1986 (Attorney Docket PR-8211).

Preferably, however, the reaction is continued with the hydrogenation step, i.e., step (b), to produce as end products, the imidazolidine compounds.

Representative compounds which can be prepared in accordance with the process described above include:
1-(3-trifluoromethyl)phenyl-3-(4-fluoro)phenyl-4-ethyl imidazolidine-2-one
1-(3-trifluoromethyl)phenyl-3-(4-fluoro)phenyl-4-ethyl-4-imidazoline-2-one
1,3-bis-(3-trifluoromethyl)phenyl-4-ethyl-4-imidazoline-2one
1,3-bis-(3-trifluoromethyl)phenyl-4-ethyl-imidazolidine-2-one
1-(3-trifluoromethyl)phenyl-3-(4-bromo)phenyl-4-ethyl imidazolidine-2-one
1-(3-trifluoromethyl)phenyl-3-(2-methyl)phenyl-4-ethyl-imidazolidine-2-one
1-(3-trifluoromethyl)phenyl-3-(4-methyl)phenyl-4-ethyl imidazolidine-2-one
1-(3-trifluoromethyl)phenyl-3-(2-methyl)phenyl-4-ethyl-4-imidazoline-2-one
1-(3-trifluoromethyl)phenyl-3-(4-methyl)phenyl-4-ethyl-4-imidazoline-2-one
1-(3-trifluoromethyl)phenyl-3-(4-chloro)phenyl-4-ethyl-4-imidazoline-2-one
1-(3-trifluoromethyl)phenyl-3-(4-bromo)phenyl-4-ethyl-4-imidazoline-2-one Examples 1–3 below illustrate the method of making the compounds of the invention.

Example 1 describes the preparation of the indicated imidazolidine-2-one beginning with the starting compounds, an anilino-2-butanone and para-fluorophenyl isocyanate.

Example 2 describes the preparation of the indicated imidazolidine beginning with an imidazoline-2-one starting material, which is produced in accordance with the first step of the process.

Example 3 describes the bromination of an imidazolidine-2-one, which has undergone the hydrogenation step. It has been found that when the imidazoline compound undergoes hydrogenation, the halogen substituent groups on the phenyl rings are sometimes cleaved. The groups can be replaced, however, by single halogenation of the imidazolidine-2-one compound obtained at the end of step (2).

Suitable analytical techniques such as IR, NMR and MS were used to identify the products.

EXAMPLE 1

Preparation of 1-(3-Trifluoromethyl)phenyl-3-(4-fluoro)phenyl-4-ethylimidazolidine-2-one 3.7 Grams (g) (0.016 mole) of 1-(3-trifluoromethyl)anilino-2-butanone and 6 milliliters (ml) of 4-fluorophenyl isocyanate (0.053 mole) were combined and heated neat on a steam bath (100° C.) for one hour. The product was extracted with ether, washed with water, dried over magnesium sulfate and stripped to dryness on a rotary evaporator. The resulting material was then extracted with ether and put through an alumina column with ether to yield 4.1 g of 1-(3-trifluoromethyl)phenyl-3-(4-fluoro)phenyl-4-ethyl-4-imidazoline-2-one, identified by standard analytical techniques.

Two grams of 1-(3-trifluoromethyl)phenyl-3-(4-fluoro)phenyl-4-ethyl-4-imidazoline-2-one (0.0057 mole) were then combined with 20 ml of ethanol and 0.2 g of 10% palladium on carbon. The mixture was shaken while hydrogen ($H_2$) at 50 psi was being added. After 3 hours, another 0.1 g of palladium on carbon were added. The mixture was allowed to shake another 5 hours when another 0.1 g of catalyst was added. After two more hours of shaking, the reaction was 97% complete. The mixture was diluted with ether, filtered through dicalite, washed with water and stripped to dryness in a rotary evaporator to yield 1.6 g of the subject product, identified as such by standard analytical techniques.

EXAMPLE 2

Preparation of 1-(3-Trifluoromethyl)phenyl-3-(4-methyl)phenyl-4-ethylimidazolidine-2-one 1.8 grams (0.005 mole) of 1-(3-trifluoromethyl)phenyl-3-(4-methyl)phenyl-4-ethyl-4-imidazoline-2-one, 20 ml ethanol and 0.5 g of 10% palladium on carbon were combined and shaken with $H_2$ at 50 psi. The reactants were shaken for 45 minutes, when another 0.2 g 10% palladium on carbon was added to the bottle. The mixture was shaken another two hours and another 0.1 g of 10% palladium on carbon was again added to the bottle. The mixture was shaken another 2 hours. The product was filtered through dicalite and the ethanol layer was stripped on a rotary evaporator, diluted with ether, washed with 2N hydrochloric acid, dried over magnesium sulfate and evaporated to dryness. 1.4 grams of product were obtained which infrared, nuclear magnetic resonance and mass spectroscopy confirmed.

EXAMPLE 3

Preparation of 1-(3-Trifluoromethyl)phenyl-3-(4-bromo)phenyl-4-ethylimidazolidine-2-one 1.4 Grams (0.004 mole) of 1-(3-trifluoromethyl)phenyl-3-phenyl-4-ethylimidazolidine-2-one and 15 ml of acetic acid were combined in a round-bottom flask fitted with a magnet. The mixture was stirred in a water bath and bromine (0.004 mole) was gradually added. After the bromine addition, the mixture was allowed to stir for two hours. The mixture was extracted with ether, washed with water and 1N sodium bicarbonate, then again with water. The product was dried over magnesium sulfate, and the ether layer evaporated to dryness. 1.1 Grams of product was obtained, which infrared, nuclear magnetic resonance and mass spectroscopy confirmed.

Compounds which have been prepared in accordance with the same general techniques of Examples 1–3 above are set forth in Tables 1 and 1a below.

TABLE 1
Imidazolidine-2-ones

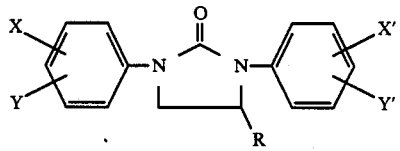

| Cmpd. No. | X | Y | X' | Y' | R | Physical Constant |
|---|---|---|---|---|---|---|
| 1 | H | 3-$CF_3$ | H | 4-F | $C_2H_5$ | m.p. 74–78° C. |
| 2 | H | 3-$CF_3$ | H | 3-$CF_3$ | $C_2H_3$ | m.p. 112–116° C. |
| 3 | H | 3-$CF_3$ | H | 4-BR | $C_2H_5$ | m.p. 100–106° C. |
| 4 | H | 3-$CF_3$ | H | 2-$CH_3$ | $C_2H_5$ | semi-solid |
| 5 | H | 3-$CF_3$ | H | 4-$CH_3$ | $C_2H_5$ | m.p. 105–106° C. |
| 6 | H | 3-$CF_3$ | H | H | $C_2H_5$ | m.p. 77–79° C. |

TABLE 1a
Imidazoline-2-ones

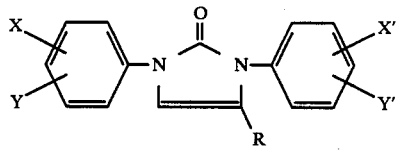

| Cmpd. No. | X | Y | X' | Y' | R | Physical m.p. °C. |
|---|---|---|---|---|---|---|
| 7 | H | 3-$CF_3$ | H | 4-F | $C_2H_5$ | 96–98 |
| 8 | H | 3-$CF_3$ | H | 3-$CF_3$ | $C_2H_5$ | 88–96 |
| 9 | H | 3-$CF_3$ | H | 4-C≡N | $C_2H_5$ | 110–112 |
| 10 | H | 3-$CF_3$ | H | 3-Cl | $C_2H_5$ | 87–89 |
| 11 | H | 3-$CF_3$ | H | 2-$CH_3$ | $C_2H_5$ | 80–86 |
| 12 | H | 3-$CF_3$ | H | 4-$CH_3$ | $C_2H_5$ | 114–116 |
| 13 | H | 3-$CF_3$ | H | 4-Cl | $C_2H_5$ | 129–130 |
| 14 | H | 3-$CF_3$ | 3-Cl | 4-Cl | $C_2H_5$ | 93–94 |
| 15 | H | 3-$CF_3$ | H | 4-Br | $C_2H_5$ | 122–125 |

In carrying out the process for making the compounds the reaction of the alkanone and the isocyanate is preferably conducted at atmospheric pressure and at temperatures of from 0° to 150° C., preferably at 90°–100° C. An excess of isocyanate is preferred to consume the water produced in the cyclization step.

No solvent is needed. However, solvents non-reactive to the intermediates can be used.

In general step (a) of the reaction can be substantially completed within about 2 hours reaction time, preferably one hour; however, the completion time may vary depending on the starting intermediates.

The hydrogenation step is conventionally carried out in a shaker which can be used to introduce hydrogen at about 50 psi into the reaction mixture. Any other means of accomplishing hydrogenation would be acceptable.

The catalyst used during the hydrogenation step can be any conventional catalyst as known to those skilled in the art; however, the preferred catalyst is palladium on carbon. Other suitable catalysts would include platinum oxide, platinum on carbon, and various palladium and platinum compounds.

The isocyanate compounds which are used as the primary reactants in the first step of the process for producing the compounds of the invention are commercially available or can be prepared by known literature procedures. The preferred isocyanate is a substituted phenyl isocyanate.

The anilino alkanones which are used as one of the primary reactants in the first step of the process can be prepared by reacting an aryl substituted anilino alcohol with di-t-butyl dicarbonate in accordance with the process disclosed in co-pending application Ser. No. 933,833, filed Nov. 24, 1986 (Attorney Docket PR-8211).

The herbicidal activity of the representative ones of the compounds of the invention is exhibited by means of tests in accordance with the following procedure.

HERBICIDAL ACTIVITY TESTS

This example offers herbicidal activity test data to show the effectiveness of the compounds of the invention. Also shown is the activity of the intermediate imidazoline-2-one compounds which can be isolated, and which are claimed in co-pending application Ser. No. 933,833, filed Nov. 24, 1986 (Attorney Docket PR-8211). The effect is observed by comparing the extent of weed control in test flats treated with the compounds against that occurring in similar control flats. The soil used in these tests was a sandy loam soil from the Livermore, Calif. area.

Also added to the soil was 17-17-17 fertilizer (N-$P_2O_5$-$K_2O$ on a weight basis), amounting to 100 ppm by weight with respect to the soil and 200 ppm Captan, a soil fungicide.

The treated soil was then placed in flats which were 3 inches deep, 6 inches wide, and 10 inches long. The soil was tamped and leveled with a row marker to impress six rows across the width of the flat. The test weeds were as follows:

| COMMON NAME | SCIENTIFIC NAME | ABR |
|---|---|---|
| GRASSES: | | |
| watergrass | Echinochloa crusgalli | WG |
| wild oat | Sorghum bicolor | WO |
| green foxtail | Setaria viridis | FT |
| yellow nutsedge | Cyperus esculentus | YNS |
| BROADLEAF WEEDS: | | |
| annual morningglory | Ipomea purpurea | AMG |
| velvetleaf | Abutilon theophrasti | VL |
| mustard | Brassica juncea | MD |

Sufficient seeds were planted to produce several seedlings per inch in each row. The flats were then placed in a greenhouse maintained at 70° to 85° F. (21° to 30° C.) and watered daily by sprinkler.

In pre-emergent testing (PES) the herbicide is applied to the soil immediately after planting of the seeds.

In post-emergent testing (POST) chemical application is made by spraying 12 days after planting. The spray solution is prepared by dissolving 84 mg of herbicide compound in 20 ml of acetone containing 0.5% Tween ®20 (polyoxyethylene sorbitan monolaurate), then adding 20 ml of water to the resulting solution. The solution is sprayed at 25 gallon/acre. Appropriate dilutions were made to achieve rates other than 4 lb/acre.

Approximately 12-14 days after treatment, the degree of weed control was estimated and recorded as percentage control compared to the growth of the same species in an untreated check flat of the same age. The rating scale ranges from 0 to 100%, where 0 equals no effect with plant growth equal to the untreated control, and 100 equals complete kill.

The results are listed in Table II below.

TABLE 2

| Cmpd. No. | Rate lb/A | Appln. Method | FT | WG | WO | AMG | VL | MD | YNS |
|---|---|---|---|---|---|---|---|---|---|
| 1 | 4.00 | PES | 100 | 100 | 80 | 60 | 100 | 100 | 0 |
|   | 4.00 | POS | 40 | 40 | 40 | 40 | 80 | 80 | 0 |
| 2 | 4.00 | PES | 10 | 5 | 0 | 0 | 0 | 80 | 0 |
|   | 4.00 | POS | 5 | 5 | 0 | 10 | 40 | 70 | 0 |
| 3 | 1.00 | PES | 100 | 20 | 15 | 70 | 10 | N | 0 |
|   | 1.00 | POS | 0 | 0 | 0 | 0 | 0 | 0 | 0 |
| 4 | 4.00 | PES | 70 | 10 | 0 | 0 | 0 | 95 | 0 |
|   | 4.00 | POS | 10 | 10 | 0 | 10 | 70 | 80 | 0 |
| 5 | 4.00 | PES | 0 | 0 | 0 | 0 | 0 | 0 | 0 |
|   | 4.00 | POS | 10 | 10 | 0 | 5 | 10 | 65 | 0 |
| 6 | 4.00 | PES | 100 | 100 | 35 | 40 | 65 | 100 | 0 |
|   | 4.00 | POS | 85 | 50 | 50 | 65 | 80 | 75 | 0 |
| 7 | 4.00 | PES | 95 | 20 | 20 | 0 | 0 | 0 | 0 |
|   | 4.00 | POS | 30 | 20 | 30 | 5 | 90 | 90 | 10 |
| 8 | 4.00 | PES | 10 | 5 | 5 | 0 | 0 | 0 | 0 |
|   | 4.00 | POS | 5 | 5 | 0 | 0 | 0 | 20 | 0 |
| 9 | 4.00 | PES | 5 | 5 | 0 | 0 | 0 | 20 | 0 |
|   | 4.00 | POS | 10 | 10 | 5 | 10 | 80 | 80 | 0 |
| 10 | 4.00 | PES | 100 | 100 | 80 | 40 | 30 | 95 | 0 |
|   | 4.00 | POS | 85 | 50 | 40 | 20 | 80 | 90 | 0 |
| 11 | 4.00 | PES | 60 | 60 | 10 | 0 | 5 | 5 | 0 |
|   | 4.00 | POS | 30 | 10 | 5 | 5 | 20 | 60 | 0 |
| 12 | 4.00 | PES | 0 | 0 | 0 | 0 | 0 | 0 | 0 |
|   | 4.00 | POS | 0 | 0 | 0 | 0 | 10 | 30 | 0 |
| 13 | 4.00 | PES | 0 | 0 | 0 | 0 | 0 | 0 | 0 |
|   | 4.00 | POS | 0 | 0 | 0 | 0 | 20 | 60 | 0 |
| 14 | 4.00 | PES | 10 | 5 | 0 | 0 | 5 | 30 | 0 |
|   | 4.00 | POS | 70 | 10 | 10 | 20 | 100 | 100 | 0 |
| 15 | 4.00 | PES | 0 | 0 | 0 | 0 | 0 | 0 | 0 |
|   | 4.00 | POS | 20 | 0 | 0 | 5 | 50 | 40 | 0 |

N = Not tested.

METHODS OF APPLICATION

The herbicidal compositions of the present invention are useful in controlling the growth of undesirable vegetation by pre-emergence or post-emergence application to the locus where control is desired, including pre-plant and post-plant soil incorporation as well as surface application. Post-emergent application is preferred. The compositions are generally embodied in formulations suitable for convenient application. Typical formulations contain additional ingredients or diluent carriers which are either inert or active. Examples of such ingredients or carriers are water, organic solvents, dust carriers, granular carriers, surface active agents, oil and water, water-oil emulsions, wetting agents, dispersing agents, and emulsifying agents. The herbicidal formulations generally take the form of dusts, emulsifiable concentrates, granules and pellets, or microcapsules.

A. DUSTS

Dusts are dense powder compositions which are intended for application in dry form. Dusts are characterized by their free-flowing and rapid setting properties so that they are not readily windborne to areas where their presence is not desired. They contain primarily an active material and a dense, free-flowing, solid carrier.

Their performance is sometimes aided by the inclusion of a wetting agent, and convenience in manufacture frequently demands the inclusion of an inert, absorptive grinding aid. For the dust compositions of this invention, the inert carrier may be either of vegetable or mineral origin, the wetting agent is preferably anionic or nonionic, and suitable absorptive grinding aids are of mineral origin.

Suitable classes of insert solid carriers for use in the dust compositions are those organic or inorganic powders which possess high bulk density and are very free-flowing. They are also characterized by low surface area and poor liquid absorptivity. Suitable grinding aids are natural clays, diatomaceous earths, and synthetic mineral fillers derived from silica or silicate. Among ionic and nonionic wetting agents, the most suitable are the members of the group known to the art as wetting agents and emulsifiers. Although solid agents are preferred because of ease of incorporation, some liquid nonionic agents are also suitable in the dust formulations.

Preferred dust carriers are micaceous talcs, pyrophyllite, dense kaolin clays, tobacco dust and ground calcium phosphate rock.

Preferred grinding aids are attapulgite clay, diactomaceous silica, synthetic fine silica and synthetic calcium and magnesium silicates.

Most preferred wetting agents are alkylbenzene and alkyl-naphthalene sulfonates, sulfated fatty alcohols, amines or acid amides, long chain acid esters of sodium isothionate, esters of sodium sulfosuccinate, sulfated or sulfonated fatty acid esters, petroleum·sulfonates, sulfonated vegetable oils, and ditertiary acetylenic glycols. Preferred dispersants are methyl cellulose, polyvinyl alcohol, lignin sulfonates, polymeric alkylnaphthalene sulfonates, sodium naphthalenesulfonate, polymethylene bisnaphthalenesulfonate, and sodium-N-methyl-N-(long chain acid) taurates.

The inert solid carriers in the dusts of this invention are usually present in concentrations of from about 30 to 90 weight percent of the total composition. The grinding aid will usually constitute 5 to 50 weight percent of the compositions, and the wetting agent will constitute from about 0 to 1.0 weight percent of the composition. Dust compositions can also contain other surfactants such as dispersing agents in concentrations of up to about 0.5 weight percent, and minor amounts of anti-caking and antistatic agents. The particle size of the carrier is usually in the range of 30 to 50 microns.

B. EMULSIFIABLE CONCENTRATES

Emulsifiable concentrates are usually solutions of the active materials in nonwater-miscible solvents together with an emulsifying agent. Prior to use, the concentrate is diluted with water to form a suspended emulsion of solvent droplets.

Typical solvents for use in emulsifiable concentrates include weed oils, chlorinated hydrocarbons, and non-water-miscible ethers, esters, and ketones.

Typical emulsifying agents are anionic or nonionic surfactants, or mixtures of the two. Examples include long-chain alkyl or mercaptan polyethoxy alcohols, alkylaryl polyethoxy alcohols, sorbitan fatty acid esters, polyoxyethylene ethers with sorbitan fatty acid esters, polyoxyethylene glycol esters with fatty or rosin acids, fatty alkylol amide condensates, calcium and amine salts of fatty alcohol sulfates, oil soluble petroleum sulfonates, or preferably mixtures of these emulsifying agents. Such emulsifying agents will comprise from about 1 to 10 weight percent of the total composition.

Thus, emulsifiable concentrates of the present invention will consist of from about 15 to about 50 weight percent active material, about 40 to 82 weight percent solvent, and about 1 to 10 weight percent emulsifier. Other additives such as spreading agents and stickers can also be included.

C. GRANULES AND PELLETS

Granules and pellets are physically stable, particulate compositions containing the active ingredients adhering to or distributed through a basic matrix of a coherent, inert carrier with microscopic dimensions. A typical particle is about 1 to 2 millimeters in diameter. Surfactants are often present to aid in leaching of the active ingredient from the granule or pellet.

The carrier is preferably of mineral origin, and generally falls within one of two types. The first are porous, absorptive, preformed granules, such as preformed and screened granular attapulgite or heat expanded, granular, screened vermiculite. On either of these, a solution of the active agent can be sprayed and will be absorbed at concentrations up to 25 weight percent of the total weight. The second, which are also suitable for pellets, are initially powdered kaolin clays, hydrated attapulgite, or bentonite clays in the form of sodium, calcium, or magnesium bentonites. Water-soluble salts, such as sodium salts, may also be present to aid in the disintegration of granules or pellets in the presence of moisture. These ingredients are blended with the active components to give mixtures that are granulated or pelleted, followed by drying, to yield formulations with the active component distributed uniformly throughout the mass. Such granules and pellets can also be made with 25 to 30 weight percent active component, but more frequently a concentration of about 10 weight percent is desired for optimum distribution. The granular compositions of this invention are most useful in a size range of 15–30 mesh.

The surfactant is generally a common wetting agent of anionic or nonionic character. The most suitable wetting agents depend upon the type of granule used. When preformed granules are sprayed with active material in liquid form the most suitable wetting agents are nonionic, liquid wetters miscible with the solvent. These are compounds most generally known in the art as emulsifiers, and comprise alkylaryl polyether alcohols, alkyl polyether alcohols, polyoxyethylene sorbitan fatty acid esters, polyethylene glycol esters with fatty or rosin acids, fatty alkylol amide condensates, oil solution petroleum or vegetable oil sulfonates, or mixtures of these. Such agents will usually comprise up to about 5 weight percent of the total composition.

When the active ingredient is first mixed with a powdered carrier and subsequently granulated, or pelleted, liquid nonionic wetters can still be used, but it is usually preferable to incorporate at the mixing stage one of the solid, powdered anionic wetting agents such as those previously listed for the wettable powders. Such agents will comprise from about 0 to 2 weight percent of the total composition.

Thus, the preferred granular or pelleted formulations of this invention comprise about 5 to 30 percent by weight active material, about 0 to 5 weight percent wetting agent, and about 65 to 95 weight percent inert material carrier, as these terms are used herein.

D. MICROCAPSULES

Microcapsules consist of fully enclosed droplets or granules containing the active materials, in which the enclosing material is an inert porous membrane, arranged to allow escape of the enclosed materials to the surrounding medium at controlled rates over a specified period. Encapsulated droplets are typically about 1 to 50 microns in diameter.

The enclosed liquid typically constitutes about 50 to 95% of the weight of the entire capsule, and may contain a small amount of solvent in addition to the active materials.

Encapsulated granules are characterized by porous membranes sealing the openings of the granule carrier pores, trapping the liquid containing the active components inside for controlled release. A typical granule size ranges from 1 millimeter to 1 centimeter in diameter. In agricultural useage, the granule size is generally about 1 to 2 ml in diameter. Granules formed by extrusion, agglomeration, or prilling are useful in the present invention as well as materials in their naturally occurring form. Examples of such carriers are vermiculite, sintered clay granules, kaolin, attapulgite clay, sawdust, and granular carbon.

Useful encapsulating materials include natural and synthetic rubbers, cellulosic materials, styrene-butadiene copolymers, polyacrylonitriles, polyacrylates, polyesters, polyamides, polyurethanes, and starch xanthates.

E. IN GENERAL

Each of the above formulations can be prepared as a package containing the herbicide together with the other ingredients of the formulation (diluents, emulsifiers, surfactants, etc.). The formulations can also be prepared by a tank mix method, in which the ingredients are obtained separately and combined at the grower site.

In general, any conventional method of application can be used. The locus of application can be soil, seeds, seedlings, or the actual plants, as well as flooded fields. Dusts and liquid compositions can be applied by the use of powder dusters, boom and hand sprayers, and spray dusters. The compositions can also be applied from airplanes as dusts and sprays because they are effective in very low dosages. In order to modify or control the growth of germinating seeds or emerging seedlings, as a typical example, the dust and liquid compositions are applied to the soil according to conventional methods and are distributed in the soil to a depth of at least one-half inch below the soil surface. It is not necessary that the phytotoxic compositions be admixed with the soil particles. Instead, these compositions can be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The herbicide compositions can also be applied to the soil through irrigation systems. According to this technique, the compositions are added directly to irrigation water immediately prior to irrigation of the field. This technique is applicable in all geographical areas regardless of rainfall, since it permits supplementation of the natural rainfall at critical stages of plant growth. In a typical application, the concentration of the herbicide composition in the irrigation water will range from about 10 to 150 parts per million by weight. The irrigation water can be applied by the use of sprinkler systems, surface furrows, or flooding. Such application is most effectively done before the weeds germinate, either early in the spring prior to germination or within two days after cultivation of the field.

The amount of the present composition which constitutes a herbicidally effective amount depends upon the nature of the seeds or plants to be controlled. The rate of application of active ingredient varies from about 0.01 to about 50 pounds per acre, preferably about 0.1 to about 25 pounds per acre with the actual amount depending on the overall cost and the desired results. It will be readily apparent to one skilled in the art that compositions exhibiting lower herbicidal activity will require a higher dosage than more active compounds for the same degree of control.

What is claimed is:

1. An imidazolidine-2-one having the formula

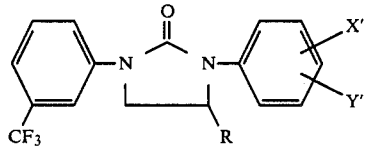

in which
X' and Y' are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups have from one to four carbon atoms; and R is selected from the group consisting of hydrogen and alkyl wherein the alkyl groups have from one to four carbon atoms.

2. A compound according to claim 1 wherein R is ethyl, X' is hydrogen and Y' is 4-fluoro.

3. A compound according to claim 1 wherein R is ethyl, X' is hydrogen and Y' is 3-trifluoromethyl.

4. A compound according to claim 1 wherein R is ethyl, X' is hydrogen and Y' is 2-methyl.

5. A compound according to claim 1 wherein R is ethyl, X' is hydrogen and Y' is 4-methyl.

6. A compound according to claim 1 wherein R is ethyl, X' is hydrogen and Y' is hydrogen.

7. A compound according to claim 1 wherein R is ethyl, X' is hydrogen and Y' is 4-bromo.

8. An herbicidal composition comprising an imidazolidine-2-one having the formula

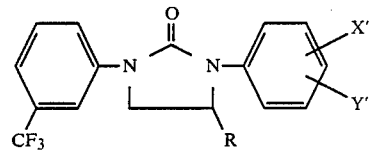

in which
X' and Y' are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups have from one to four carbon atoms; and R is selected from the group consisting of hydrogen and alkyl wherein the alkyl groups have from one to four carbon atoms.

9. A composition according to claim 8 wherein R is ethyl, X' is hydrogen and Y' is 4-fluoro.

10. A composition according to claim 8 wherein R is ethyl, X' is hydrogen and Y' is 3-trifluoromethyl.

11. A composition according to claim 8 wherein R is ethyl, X' is hydrogen and Y' is 2-methyl.

12. A composition according to claim 8 wherein R is ethyl, X' is hydrogen and Y' is 4-methyl.

13. A composition according to claim 8 wherein R is ethyl, X' is hydrogen and Y' is hydrogen.

14. A composition according to claim 8 wherein R is ethyl, X' is hydrogen and Y' is 4-bromo.

15. A method for controlling undesirable weed pests which comprises applying to the locus where control is desired a herbicidally effective amount of an imidazolidine-2-one having the formula

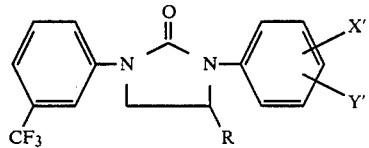

in which
X' and Y' are the same or different and are selected from the group consisting of trifluoromethyl, chloro, bromo, fluoro, hydrogen, cyano, alkyl, thioalkyl, halothioalkyl, alkoxy and sulfonylalkyl, wherein the alkyl groups have from one to four carbon atoms; and R is selected from the group consisting of hydrogen and alkyl wherein the alkyl groups have from one to four carbon atoms.

16. A method according to claim 15 wherein R is ethyl, X' is hydrogen and Y' is 4-fluoro.

17. A method according to claim 15 wherein R is ethyl, X' is hydrogen and Y' is 3-trifluoromethyl.

18. A method according to claim 15 wherein R is ethyl, X' is hydrogen and Y' is 2-methyl.

19. A method according to claim 15 wherein R is ethyl, X' is hydrogen and Y' is 4-methyl.

20. A method according to claim 15 wherein R is ethyl, X' is hydrogen and Y' is hydrogen.

21. A method according to claim 15 wherein R is ethyl, X' is hydrogen and Y' is 4-bromo.

* * * * *

UNITED STATES PATENT AND TRADEMARK OFFICE
CERTIFICATE OF CORRECTION

PATENT NO. : 4,744,813

DATED : May 17, 1988

INVENTOR(S) : Eugene G. Teach

It is certified that error appears in the above-identified patent and that said Letters Patent is hereby corrected as shown below:

In Claim 8, last line, before the period please insert the phrase — and an inert diluent carrier —.

Signed and Sealed this

Thirty-first Day of January, 1989

Attest:

DONALD J. QUIGG

Attesting Officer

Commissioner of Patents and Trademarks